(12) United States Patent
Koyanagi et al.

(10) Patent No.: US 6,624,179 B1
(45) Date of Patent: Sep. 23, 2003

(54) GEOMETRICAL ISOMERS OF ACRYLONITRILE COMPOUNDS, MIXTURE THEREOF, AND PROCESS FOR PRODUCING THESE

(75) Inventors: Toru Koyanagi, Kusatsu (JP); Yuji Nakamura, Kusatsu (JP); Masayuki Morita, Kusatsu (JP); Tsuyoshi Ueda, Kusatsu (JP); Akihiro Hisamatsu, Kusatsu (JP); Mayumi Kanamori, Kusatsu (JP)

(73) Assignee: Ishihara Sangyo Kaisha Ltd., Osaka (JP)

( * ) Notice: Subject to any disclaimer, the term of this patent is extended or adjusted under 35 U.S.C. 154(b) by 0 days.

(21) Appl. No.: 10/030,122

(22) PCT Filed: Jul. 26, 2000

(86) PCT No.: PCT/JP00/04996
§ 371 (c)(1),
(2), (4) Date: Jan. 24, 2002

(87) PCT Pub. No.: WO01/09086
PCT Pub. Date: Feb. 8, 2001

(30) Foreign Application Priority Data

Jul. 30, 1999 (JP) .......................................... 11-217082

(51) Int. Cl.⁷ .............................................. A61K 31/44
(52) U.S. Cl. ........................ 514/336; 514/357; 514/438; 514/520; 546/281.4; 546/330; 549/76; 558/303
(58) Field of Search ................................ 514/520, 336, 514/357, 438; 558/303; 546/281.4, 330; 549/76

(56) References Cited

U.S. PATENT DOCUMENTS 6,187,944 B1 * 2/2001 Koyanagi et al. ........... 558/397

FOREIGN PATENT DOCUMENTS

WO  98/35935  8/1998

* cited by examiner

Primary Examiner—Joseph K. McKane
Assistant Examiner—Robert Shiao
(74) Attorney, Agent, or Firm—Oblon, Spivak, McClelland, Maier & Neustadt, P.C.

(57) ABSTRACT

A geometrical isomer of an acrylonitrile compound represented by the formula (I) or of its salt, or a mixture thereof:

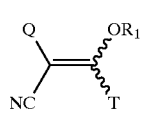

(I)

[wherein T is phenyl or pyridyl, which is substituted by $R_2$, Q is phenyl, thienyl, pyridyl or benzyl, which may be substituted by $R_3$, $R_1$ is —C(=O)$R_4$ or —C(=S)$R_4$, $R_4$ is alkyl, alkenyl, alkynyl, alkoxy, alkenyloxy, alkynyloxy, alkylthio, alkenylthio, alkynylthio, cycloalkyl, cycloalkyloxy, cycloalkylthio, —N($R_5$)$R_6$, phenyl, phenoxy, phenylthio, benzyl, benzyloxy, benzylthio, —J, —O—J or —S—J], wherein the geometrical isomer has a longer retention time when analyzed by reversed phase liquid chromatography in which a packing comprising silica having chemically bonded thereto an alkyl group selected from trimethyl, octyl and octadecyl, is used as the stationary phase, and a polar solvent selected from water, methanol and acetonitrile, is used as the mobile phase, and the geometrical isomer mixture contains such geometrical isomer in a larger proportion.

14 Claims, No Drawings

GEOMETRICAL ISOMERS OF ACRYLONITRILE COMPOUNDS, MIXTURE THEREOF, AND PROCESS FOR PRODUCING THESE

TECHNICAL FIELD

The present invention relates to geometrical isomers of acrylonitrile compounds useful as active ingredients for pesticides, a mixture thereof and a process for their production.

BACKGROUND ART

WO98/35935 discloses acrylonitrile compounds or their salts, and it is disclosed that such compounds have geometrical isomers. However, no specific method is disclosed, whereby one geometric isomer compound of an acrylonitrile compound represented by the following formula (I) or of its salt, is produced in a larger proportion than the other geometrical isomer compound.

DISCLOSURE OF THE INVENTION

The present inventors have conducted various studies on a method whereby one geometrical isomer compound is produced in a larger proportion than the other geometrical isomer compound, and as a result, the present invention has been accomplished. Namely, the present invention provides a geometrical isomer of an acrylonitrile compound represented by the formula (I) or of its salt, or a mixture thereof:

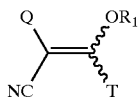

(I)

[wherein T is phenyl which is substituted by $R_2$, or pyridyl which is substituted by $R_2$, Q is phenyl which may be substituted by $R_3$, thienyl which may be substituted by $R_3$, pyridyl which may be substituted by $R_3$, or benzyl which may be substituted by $R_3$, $R_1$ is —C(=O)$R_4$ or —C(=S)$R_4$, each of $R_2$ and $R_3$ is halogen, alkyl which may be substituted, alkenyl which may be substituted, alkynyl which may be substituted, alkoxy which may be substituted, alkenyloxy which may be substituted, alkynyloxy which may be substituted, alkylthio which may be substituted, alkylsulfinyl which may be substituted, alkylsulfonyl which may be substituted, alkenylthio which may be substituted, alkenylsulfinyl which may be substituted, alkenylsulfonyl which may be substituted, alkynylthio which may be substituted, alkynylsulfinyl which may be substituted, alkynylsulfonyl which may be substituted, nitro, cyano, phenyl which may be substituted, phenoxy which may be substituted, phenylthio which may be substituted, phenylsulfinyl which may be substituted, phenylsulfonyl which may be substituted, benzyl which may be substituted, benzyloxy which may be substituted, benzylthio which may be substituted, or benzoyl which may be substituted, $R_4$ is alkyl which may be substituted, alkenyl which may be substituted, alkynyl which may be substituted, alkoxy which may be substituted, alkenyloxy which may be substituted, alkynyloxy which may be substituted, alkylthio which may be substituted, alkenylthio which may be substituted, alkynylthio which may be substituted, cycloalkyl, cycloalkyloxy, cycloalkylthio, —N($R_5$)$R_6$, phenyl which may be substituted, phenoxy which may be substituted, phenylthio which may be substituted, benzyl which may be substituted, benzyloxy which may be substituted, benzylthio which may be substituted, —J, —O—J or —S—J, each of $R_5$ and $R_6$ is hydrogen, alkyl or alkoxy, J is a 5- or 6-membered heterocyclic group (the heterocyclic group may be substituted) having from 1 to 4 hetero atoms of at least one type selected from the group consisting of O, S and N, provided that the following compounds are excluded: (1) a compound wherein T is phenyl which is substituted by $R_2$, Q is thienyl which may be substituted by $R_3$, $R_1$ is —C(=O)$R_4$, and $R_4$ is alkyl which may be substituted, alkenyl which may be substituted, alkynyl which may be substituted, alkoxy which may be substituted, alkenyloxy which may be substituted, alkynyloxy which may be substituted, cycloalkyl, cycloalkyloxy, —N($R_5$)$R_6$, phenyl which may be substituted, phenoxy which may be substituted, phenylthio which may be substituted, benzyl which may be substituted, benzyloxy which may be substituted, benzylthio which may be substituted, —J, —O—J or —S—J, (2) a compound wherein T is phenyl which is substituted by $R_2$, Q is thienyl which may be substituted by $R_3$, $R_1$ is —C(=S)$R_4$, and $R_4$ is —N($R_5$)$R_6$, (3) a compound wherein T is pyridyl which is substituted by $R_2$, Q is thienyl which may be substituted by $R_3$, or pyridyl which may be substituted by $R_3$, $R_1$ is —C(=O)$R_4$, and $R_4$ is alkyl, (4) α-(3,5-dimethoxyphenyl)-β-(2-methoxy-4-methylphenyl)-β-acetoxyacrylonitrile, and (5) α-(3,5-dimethoxyphenyl)-β-(2,6-dimethoxy-4-methylphenyl)-β-acetoxyacrylonitrile], wherein the geometrical isomer has a longer retention time when analyzed by reversed-phase liquid chromatography in which a packing comprising silica having chemically bonded thereto an alkyl group selected from trimethyl, octyl and octadecyl, is used as the stationary phase, and a polar solvent selected from water, methanol and acetonitrile, is used as the mobile phase, and the geometrical isomer mixture contains such geometrical isomer in a larger proportion; and a process for their production.

The substituent for the alkyl which may be substituted, the alkenyl which may be substituted, the alkynyl which may be substituted, the alkoxy which may be substituted, the alkenyloxy which may be substituted, the alkynyloxy which may be substituted, the alkylthio which may be substituted, the alkylsulfinyl which may be substituted, the alkylsulfonyl which may be substituted, the alkenylthio which may be substituted, the alkenylsulfinyl which may be substituted, the alkenylsulfonyl which may be substituted, the alkynylthio which may be substituted, the alkynylsulfinyl which may be substituted and the alkynylsulfonyl which may be substituted, for $R_2$ or $R_3$, and for the alkyl which may be substituted, the alkenyl which may be substituted, the alkynyl which may be substituted, the alkoxy which may be substituted, the alkenyloxy which may be substituted, the alkynyloxy which may be substituted, the alkylthio which may be substituted, the alkenylthio which may be substituted and the alkynylthio which may be substituted, for $R_4$, may, for example, be halogen, alkoxy, haloalkoxy, alkoxycarbonyl, alkylthio, alkylsulfinyl, alkylsulfonyl, haloalkylthio, haloalkylsulfinyl, haloalkylsulfonyl, amino, monoalkylamino, dialkylamino, nitro or cyano. The number of substituents may be one or more, and when it is two or more, they may be the same or different.

The substituent for the phenyl which may be substituted, the phenoxy which may be substituted, the phenylthio which may be substituted, the phenylsulfinyl which may be substituted, the phenylsulfonyl which may be substituted, the benzyl which may be substituted, the benzyloxy which may be substituted, the benzylthio which may be substituted and the benzoyl which may be substituted, for $R_2$ or $R_3$, for the phenyl which may be substituted, the phenoxy which may be substituted, the phenylthio which may be substituted, the benzyl which may be substituted, the benzyloxy which may be substituted and the benzylthio which may be substituted, for $R_4$, and for the heterocyclic group for J, may, for example, be halogen, alkyl, haloalkyl, alkoxy, haloalkoxy, nitro, cyano, alkylthio, alkylsulfinyl, alkylsulfonyl, haloalkylthio, haloalkylsulfinyl, haloalkylsulfonyl, amino, monoalkylamino or dialkylamino. The number of substituents may be one or more, and when it is two or more, they may be the same or different.

The heterocyclic group for J may, for example, be furyl, thienyl, pyrrolyl, pyrazolyl, imidazolyl, triazolyl, tetrazolyl, oxazolyl, isoxazolyl, thiazolyl, isothiazoly, pyridyl, pyrimidinyl, 1-pyrrolidinyl, 1-piperidinyl or 4-morpholino.

The alkyl or alkyl moiety contained in $R_2$, $R_3$, $R_4$, $R_5$ or $R_6$, may, for example, be straight chain or branched one having from 1 to 6 carbon atoms, such as methyl, ethyl, propyl, isopropyl, butyl, tert-butyl, pentyl or hexyl. The alkenyl, alkynyl, alkenyl moiety or alkynyl moiety contained in $R_2$, $R_3$ or $R_4$, may, for example, be straight chain or branched one having from 2 to 6 carbon atoms, such as vinyl, allyl, butadienyl, isopropenyl, ethynyl, propynyl or 2-penten-4-ynyl. The cycloalkyl or cycloalkyl moiety contained in $R_4$, may, for example, be one having from 3 to 6 carbon atoms, such as cyclopropyl, cyclopentyl or cyclohexyl.

The halogen or the halogen as a substituent contained in $R_2$, $R_3$, $R_4$ or J, may, be an atom of fluorine, chlorine, bromine or iodine. The number of halogens as substituents may be one or more, and when it is two or more, they may be the same or different.

The acrylonitrile compound of the formula (I) is capable of forming a salt. Such a salt may be any salt so long as it is acceptable for agriculture. For example, it may be an inorganic salt such as a hydrochloride, a sulfate or a nitrate, or an organic salt such as an acetate or a methane sulfonate.

In the present invention, the geometrical isomer having a longer retention time is a compound corresponding to a latter peak among two peaks (one for the E-isomer, and the other for the Z-isomer) showing the acrylonitrile compound represented by the above formula (I) or its salt, when a geometrical isomer mixture (the mixture of the E-isomer and the Z-isomer) of the acrylonitrile compound represented by the above formula (I) or its salt, is analyzed by reversed-phase liquid chromatography (such as HPLC) under the above-mentioned conditions. Further, the geometrical isomer mixture containing the geometrical isomer having a longer retention time in a larger proportion is meant for a geometrical isomer mixture, of which, among the above two peaks, the area of the latter peak is larger than the area of the former peak. Further, the geometrical isomer mixture of the present invention preferably contains at least 60%, more preferably at least 80%, of the geometrical isomer having a longer retention time. More specifically, the area ratio of the above two peaks, i.e. the former peak to the latter peak, is preferably 40:60 or higher, more preferably 20:80 or higher.

The geometrical isomer having a longer retention time, or the geometrical isomer mixture containing such a geometric cal isomer in a larger proportion, of the present invention, can be produced by the following reaction (A), (B) or (C).

(A)

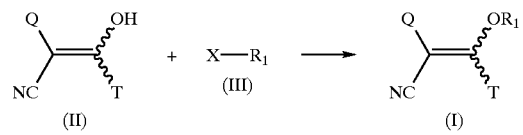

(wherein T, Q and $R_1$ are as defined above, and X is halogen.)

The compound represented by the formula (II) can be produced by a method disclosed in WO98/35935, or by the method which will be described hereinafter.

The reaction (A) is carried out usually in the presence of a base and a solvent. As the base, one or more are suitably selected from, for example, an alkali metal such as sodium or potassium; an alkali metal carbonate such as sodium carbonate or potassium carbonate; an alkali metal hydrogencarbonate such as sodium hydrogencarbonate or potassium hydrogencarbonate; an alkali metal hydride such as sodium hydride or potassium hydride, and a tertiary amine such as trimethylamine, triethylamine, pyridine, 4-dimethylaminopyridine or 1,8-diazabicyclo[5.4.0]-7-undecene. A preferred base is an alkali metal carbonate, an alkali metal hydride or a tertiary amine. A more preferred base is an alkali metal carbonate or a tertiary amine. Among them, sodium carbonate, potassium carbonate or 1,8-diazabicyclo[5.4.0]-7-undecene is particularly preferred. The amount of the base to be used, is usually from 1.0 to 2.5 equivalents, preferably from 1.0 to 1.2 equivalents, based on the compound of the formula (II).

As the solvent, any solvent may be employed so long as it is inert to the reaction. For example, one or more are suitably selected from, for example, an aliphatic hydrocarbon such as chloroform, dichloromethane, dichloroethane or trichloroethane; an ether such as dioxane, tetrahydrofuran or diethyl ether; an ester such as methyl acetate or ethyl acetate; a polar aprotic solvent such as dimethylsulfoxide, sulfolane, dimethylacetamide, dimethylformamide, N-methylpyrrolidone, pyridine, acetonitrile or propionitrile; and a ketone such as acetone or methyl ethyl ketone. A preferred solvent is an aliphatic hydrocarbon, an ether, a polar aprotic solvent or a ketone. A more preferred solvent is a polar aprotic solvent or a ketone. Among them, dimethylformamide, acetonitrile, acetone or methyl ethyl ketone is particularly preferred.

The reaction temperature for the reaction (A) is usually from −80 to +150° C., preferably from −50 to +120° C., more preferably from 0 to 80° C., and the reaction time is usually from 0.1 to 48 hours, preferably from 0.2 to 24 hours, more preferably from 0.2 to 10 hours.

(B) A geometrical isomer having a shorter retention time when analyzed by the reversed-phase liquid chromatography, or a geometrical isomer mixture containing such geometrical isomer in a larger proportion, is isomerized under irradiation with light. The geometrical isomer having a shorter retention time, or the geometrical isomer mixture, can be produced by a method disclosed in WO98/35935.

The reaction (B) consists essentially of isomerizing the geometrical isomer having a shorter retention time under irradiation with light to the geometrical isomer having a longer retention time. It may be represented by the following formula.

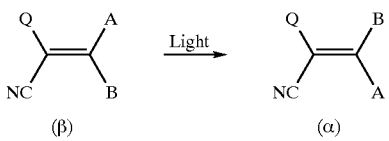

(wherein Q is as defined above, one of A and B is T, and the other is $R_1$ (T and $R_1$ are as defined above), β represents a geometrical isomer having a shorter retention time, and α represents a geometrical isomer having a longer retention time.)

The reaction (B) is carried out under irradiation with light, more specifically under irradiation with ultraviolet rays. The light source is not particularly limited. For example, a sunbeam, a mercury lamp, a laser, a deuterium lamp or a metal halide lamp may be mentioned. Among them, a sunbeam or a mercury lamp is preferred.

The reaction (B) may be carried out in the presence of a solvent, as the case requires. As the solvent, any solvent may be employed so long as it is inert to the reaction. For example, one or more are suitably selected from e.g. an aromatic hydrocarbon such as benzene, toluene, xylene or chlorobenzene; an aliphatic hydrocarbon such as hexane or cyclohexane; an ether such as dioxane, tetrahydrofuran or diethyl ether; an ester such as methyl acetate or ethyl acetate; a polar aprotic solvent such as dimethylsulfoxide, sulfolane, dimethylacetamide, dimethylformamide, N-methylpyrrolidone, pyridine, acetonitrile or propionitrile; a ketone such as acetone or methyl ethyl ketone; an amine such as monomethylamine, dimethylamine or triethylamine; and an organic acid such as acetic acid or propionic acid. A preferred solvent is a non-polar solvent such as a aromatic hydrocarbon or an aliphatic hydrocarbon. A more preferred solvent is benzene, toluene or hexane.

The reaction (B) i.e. the above isomerization is not influenced by a temperature, and the reaction temperature may be at any level. Thus, the reaction may be carried out usually in the vicinity of room temperature, specifically from 0 to 30° C. With respect to the reaction time for the reaction (B), the isomerization can be carried out usually from 0.5 to 24 hours, preferably from 1 to 8 hours, if the concentration of the geometrical isomer having a shorter retention time or of the geometrical isomer mixture containing such a geometrical isomer having a shorter retention time in a larger proportion, is, for example, from $10^{-3}$ to 1 mol/l.

The reaction (B) is carried out preferably in the presence of an inert gas, and as such an inert gas, nitrogen, helium or argon may be mentioned.

(C)

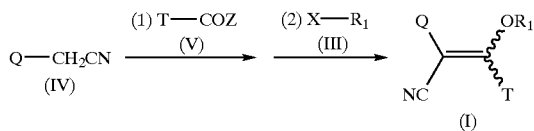

(wherein T, Q, $R_1$ and X are as defined above, and Z is halogen or alkoxy.)

Steps (1) and (2) in the reaction (C) can be carried out continuously in the same reactor.

The reaction (C) is carried out usually in the presence of a base and a solvent.

As the base, one or more are suitably selected from, for example, an alkali metal such as sodium or potassium; an alkali metal hydride such as sodium hydride or potassium hydride; a tertiary amine such as trimethylamine, triethylamine, pyridine, 4-dimethylaminopyridine or 1,8-diazabicyclo[5.4.0]-7-undecene; and an organic lithium such as methyl lithium, n-butyl lithium, tert-butyl lithium or phenyl lithium. A preferred base is a strong base, more specifically an alkali metal hydride or an organic lithium. A more preferred base is an alkali metal hydride. Among them, sodium hydride or potassium hydride is particularly preferred. The amount of the base to be used is usually from 2.0 to 2.5 equivalents, preferably from 2.1 to 2.2 equivalents, based on the compound of the formula (IV). The base may be added suitably in the step (2), whereby the reaction may further be accelerated.

As the solvent, any solvent may be employed so long as it is inert to the reaction. For example, one or more are suitably selected from, for example, an aromatic hydrocarbon such as benzene, toluene or xylene; an ether such as dioxane, tetrahydrofuran or diethyl ether; an ester such as methyl acetate or ethyl acetate; a polar aprotic solvent such as dimethylsulfoxide, sulfolane, dimethylacetamide, dimethylformamide, N-methylpyrrolidone, pyridine, acetonitrile or propionitrile; and a ketone such as acetone or methyl ethyl ketone. A preferred solvent is an aromatic hydrocarbon, an ether or a polar aprotic solvent such as dimethylacetamide or dimethylformamide. A more preferred solvent is an ether or a polar aprotic solvent such as dimethylacetamide or dimethylformamide. Among them, tetrahydrofuran or dimethylformamide is particularly preferred. The solvent may be added suitably at the time of carrying out the step (2).

The reaction (C) is carried out via an intermediate compound formed by step (1). The intermediate compound varies depending upon the type of the base used. When an alkali metal-containing base or a tertiary amine is used, the reaction is carried out via a compound represented by the formula:

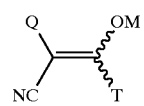

(wherein T and Q are as defined above, and M is an alkali metal or a tertiary amine conjugated acid), and when other base is used, the reaction is carried out via a compound represented by the formula:

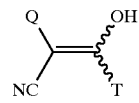

(wherein T and Q are as defined above).

The reaction temperature of the reaction (C) is usually from −80 to +150° C., preferably from −50 to +120° C., more preferably from 0 to 80° C. The reaction time is usually from 0.1 to 48 hours, preferably from 0.5 to 24 hours, more preferably from 1 to 6 hours.

The geometrical isomer mixture produced by the above reaction (A), (B) or (C) may be purified to increase the ratio of the geometrical isomer having a longer retention time. The purification method may be recrystallization which is carried out in the presence of a solvent. The recrystallization can be carried out under heating, if necessary. As the solvent, one or more are suitably selected from, for example, an aromatic hydrocarbon such as benzene, toluene or chlorobenzene; an aliphatic hydrocarbon such as hexane, isoparaffin or cyclohexane; an ether such as dioxane, tetrahydrofuran or diethyl ether; an ester such as methyl acetate or ethyl acetate; an alcohol such as methanol, ethanol or isopropanol; a polar aprotic solvent such as acetonitrile or propionitrile; and a ketone such as acetone or methyl ethyl ketone. A preferred solvent is an aliphatic hydrocarbon or an alcohol.

An example for the method for producing the compound represented by the above formula (II) will be described.

(D)

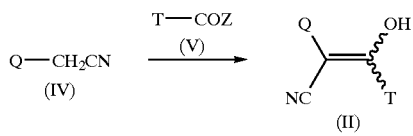

(wherein T, Q and Z are as defined above.)

The reaction (D) is carried out usually in the presence of a base and a solvent.

As the base, one or more are suitably selected from, for example, an alkali metal such as sodium or potassium; an alkali metal alcoholate such as sodium methylate, sodium ethylate or potassium tertiary butyrate; an alkali metal hydride such as sodium hydride or potassium hydride; and an organic lithium such as methyl lithium, n-butyl lithium, tert-butyl lithium or phenyl lithium. A preferred base is an alkali metal alcoholate or an alkali metal hydride. Among them, potassium tertiary butyrate, sodium hydride or potassium hydride is preferred. The amount of the base to be used, is usually from 2.0 to 2.5 equivalents, preferably from 2.0 to 2.2 equivalents, based on the compound of the formula (IV).

As the solvent, any solvent may be employed so long as it is inert to the reaction. For example, one or more are suitably selected from, for example, an aromatic hydrocarbon such as benzene, toluene, xylene or chlorobenzene; an ether such as dioxane, tetrahydrofuran or diethyl ether; an alcohol such as methanol, ethanol, propanol or tert-butanol; and a polar aprotic solvent such as dimethylformamide. However, when Z is halogen, it is not desirable to use an alcohol. A preferred solvent is an aromatic hydrocarbon, an ether or a polar aprotic solvent. A more preferred solvent is an ether or a polar aprotic solvent. Among them, tetrahydrofuran or dimethylformamide is particularly preferred.

The reaction temperature of the reaction (D) is usually from −80 to +150° C., preferably from −50 to +120° C., more preferably from 0 to 120° C. The reaction time is usually from 0.1 to 48 hours, preferably from 0.5 to 24 hours, more preferably from 0.5 to 10 hours.

The geometrical isomer having a longer retention time and the geometrical isomer mixture containing such geometrical isomer in a larger proportion, of the present invention (hereinafter referred to generally as the compounds of the present invention) are useful as active ingredients of excellent pesticides. They are particularly useful as active ingredients of pesticides such as an insecticide, a miticide, a nematicide, a soil pesticide, a fungicide and a marine antifouling agent.

Preferred embodiments of pesticides containing the compounds of the present invention will now be described. Firstly, pesticides such as an insecticide, a miticide, a nematicide, a soil pesticide and a fungicide, will be described.

The pesticides containing the compounds of the present invention are useful as an insecticide, a miticide, a nemati-cide and a soil pesticide (hereinafter referred to as insect pest control agents), and they are effective for controlling plant parasitic mites such as two-spotted spider mite (*Tetranychus urticae*), carmine spider mite (*Tetranychus cinnabarinus*), kanzawa spider mite (*Tetranychus kanzawai*), citrus red mite (*Panonychus citri*), European red mite (*Panonychus ulmi*), broad mite (*Polyphagotarsonemus latus*), pink citrus rust mite (*Aculops pelekassi*) and bulb mite (*Rhizoglyphus echinopus*); animal parasitic mites such as Ixodes; aphids such as green peach aphid (*Myzus persicae*) and cotton aphid (*Aphis gossypii*); agricultural insect pests such as diamondback moth (*Plutella xylostella*), cabbage armyworm (*Mamestra brassicae*), common cutworm (*Spodoptera litura*), codling moth (*Laspeyresia pomonella*), bollworm (*Heliothis zea*), tobacco budworm (*Heliothis virescens*), gypsy moth (*Lymantria dispar*), rice leafroller (*Cnaphalocrocis medinalis*), Adoxophyes sp., colorado potato beetle (*Leptinotarsa decemlineata*), cucurbit leaf beetle (*Aulacophora femoralis*), boll weevil (*Anthonomus grandis*), planthoppers, leafhoppers (Circulifer sp.), scales, bugs, whiteflies, thrips, grasshoppers, anthomyiid flies, scarabs, black cutworm (*Agrotis ipsilon*), cutworm (*Agrotis segetum*) and ants; plant parasitic nematodes such as root-knot nematodes, cyst nematodes, root-lesion nematodes, rice white-tip nematode (*Aphelenchoides besseyi*), strawberry bud nematode (*Nothotylenchus acris*), pine wood nematode (*Bursaphelenchus lignicolus*); gastropods such as slugs and snails; soil pests such as isopods such as pillbugs (*Armadilidium vulgare*) and pillbugs (*Porcellio scaber*); hygienic insect pests such as tropical rat mite (*Ornithonyssus bacoti*), cockroachs, housefly (*Musca domestica*) and house mosquto (*Culex pipiens*); stored grain insect pests such as angoumois grai moth (*Sitotroga cerealella*), adzuki bean weevil (*Callosobruchus chinensis*), red flour beetle (*Tribolium castaneum*) and mealworms; household goods insect pests such as casemaking clothes moth (*Tinea pellionella*), black carpet beetle (*Anthrenus scrophularidae*) and subterranean termites; domestic mites such as mold mite (*Tyrophagus putrescentiae*), *Dermatophagoides farinae* and *Chelacaropsis moorei*; and others such as fleas, lice and flies, which are parasitic to e.g. domestic animals. Among them, the insect pest control agents containing the compounds of the present invention are particularly effective for controlling plant parasitic mites, animal parasitic mites, agricultural insect pests, hygienic insect pests, household goods insect pests, domestic mites or the like. Further, they are effective against insect pests having acquired resistance to organophosphorus, carbamate and/or synthetic pyrethroid insecticides. Moreover, the compounds of the present invention have excellent systemic properties, and by the application of the compounds of the present invention to solid treatment, not only noxious insects, noxious mites, noxious nematodes, noxious gastropods and noxious isopods in soil but also foliage pests can be controlled.

Further, the pesticides containing compounds of the present invention are useful as fungicides. For example, they are effective for controlling diseases, such as blast (*Pyricularia oxyzae*), sheath blight (*Rhizoctonia solani*) and brown spot (*Cochliobolus miyabeanus*) against rice; powdery mildew (*Erysiphe graminis*), scab (*Gibberella zeae*), rust (*Puccinia striiformis. P. coronata, P. graminis, P. recondita, P. hordei*), snow blight (Typhula sp., *Micronectriella nivalis*), loose smut (*Ustilago tritici, U. nuda*), eye spot (*Pseudocercosporella herpotrichoides*), leaf blotch (*Septoria tritici*) and glume blotch (*Leptosphaeria nodorum*) against cereals; melanose (*Diaporthe citri*) and scab (*Elsinoe fawcetti*) against citrus; blossom blight (*Sclerotinia mali*), powdery mildew (*Podosphaera eucotricha*), alternaria blotch (*Alternaria mali*) and scab (*Venturia inaequalis*) against apples; scab (*Venturia ashicola*) and black spot (*Alternaria kikuchiana*) against pears; brown rot (*Monilinia fructicola*), scab (*Cladosporium carpophilum*) and phomopsis rot (Phomopsis sp.) against peaches; anthracnose (*Elsinoe ampelina*) ripe rot (*Glomerella cingulata*), powdery mildew (*Uncinula necator*) and downy mildew (*Plasmopara viticola*) against grapes; anthracnose (*Gloeosporium kaki*) and angular leaf spot (*Cercospora kaki*) against Japanese persimon; anthracnose (*Colletotrichum lagenarium*), powdery mildew (*Sphaerotheca fuliginia*), gummy stem blight (*Mycosphacrella melonis*) and downy mildew (*Pseudopernospora cubensis*) against cucurbits; early blight (*Alternaria solani*), leaf mold (*Cladosporium fulvum*) and late blight (*Phytophthora infestans*) against tomatoes; alternaria leaf spot (*Alternaria brassicae*) against crucifer; early blight (*Alternaria solani*) and late blight (*Phytophthora infestans*) against potatoes; powdery mildew (*Sphaerotheca humuli*) against strawberry; gray mold (*Botrytis cinerea*) and sclerotinial rot (*Sclerotinia sclerotiorum*) against various crop plants. Further, they are effective also for controlling soil diseases brought about by plant pathogenic fungi such as Fusarium sp., Pythium sp., Rhizoctonia sp., Verticillium sp., and Plasmodiophora sp.

Another preferred embodiments of the pesticides containing compounds of the present invention may be agricultural and horticultural pesticides which collectively control the above-mentioned plant parasitic mites, agricultural insect pests, plant parasitic nematodes, gastropods, soil pests, various diseases and various soil diseases.

The pesticide such as the insect pests control agent or the fungicide containing the compound of the present invention, is usually formulated by mixing the compound with various agricultural adjuvants and used in the form of a formulation such as a dust, granules, water-dispersible granules, a wettable powder, a water-based suspension concentrate, an oil-based suspension concentrate, water soluble granules, an emulsifiable concentrate, a paste, an aerosol or an ultra low-volume formulation. However, so long as it is suitable for the purpose of the present invention, it may be formulated into any type of formulation which is commonly used in this field. Such agricultural adjuvants include solid carriers such as diatomaceous earth, slaked lime, calcium carbonate, talc, white carbon, kaoline, bentonite, a mixture of kaolinite and sericite, clay, sodium carbonate, sodium bicarbonate, mirabilite, zeolite and starch; solvents such as water, toluene, xylene, solvent naphtha, dioxane, acetone, isophorone, methyl isobutyl ketone, chlorobenzene, cyclohexane, dimethylsulfoxide, dimethylformamide, dimethylacetamide, N-methyl-2-pyrrolidone, and alcohol; anionic surfactants and spreaders such as a salt of fatty acid, a benzoate, an alkylsulfosuccinate, a dialkylsulfosuccinate, a polycarboxylate, a salt of alkylsulfuric acid ester, an alkyl sulfate, an alkylaryl sulfate, an alkyl diglycol ether sulfate, a salt of alcohol sulfuric acid ester, an alkyl sulfonate, an alkylaryl sulfonate, an aryl sulfonate, a lignin sulfonate, an alkyldiphenyl ether disulfonate, a polystyrene sulfonate, a salt of alkylphosphoric acid ester, an alkylaryl phosphate, a styrylaryl phosphate, a salt of polyoxyethylene alkyl ether sulfuric acid ester, a polyoxyethylene alkylaryl ether sulfate, a salt of polyoxyethylene alkylaryl ether sulfuric acid ester, a polyoxyethylene alkyl ether phosphate, a salt of polyoxyethylene alkylaryl phosphoric acid ester, and a salt of a condensate of naphthalene sulfonate with formalin; nonionic surfactants and spreaders such as a sorbitan fatty acid ester, a glycerin fatty acid ester, a fatty acid polyglyceride, a fatty acid alcohol polyglycol ether, acetylene glycol, acetylene alcohol, an oxyalkylene block polymer, a polyoxyethylene alkyl ether, a polyoxyethylene alkylaryl ether, a polyoxyethylene styrylaryl ether, a polyoxyethylene glycol alkyl ether, a polyoxyethylene fatty acid ester, a polyoxyethylene sorbitan fatty acid ester, a polyoxyethylene glycerin fatty acid ester, a polyoxyethylene hydrogenated castor oil, and a polyoxypropylene fatty acid ester; and vegetable and mineral oils such as olive oil, kapok oil, castor oil, palm oil, camellia oil, coconut oil, sesame oil, corn oil, rice bran oil, peanut oil, cottonseed oil, soybean oil, rapeseed oil, linseed oil, tung oil, and liquid paraffins. Such adjuvants may be selected for use among those known in this field, so long as the purpose of the present invention can thereby be accomplished. Further, various additives which are commonly used, such as a filler, a thickener, an anti-settling agent, an anti-freezing agent, a dispersion stabilizer, a phytotoxicity reducing agent, and an anti-mold agent, may also be employed.

The weight ratio of the compound of the present invention to the various agricultural adjuvants is usually from 0.001:99.999 to 95:5, preferably from 0.005:99.995 to 90:10.

In the actual application of such a formulation, it may be used as it is, or may be diluted to a predetermined concentration with a diluent such as water, and various extenders may be added thereto, as the case requires.

The application of the pesticide such as the insect pest control agent or the fungicide containing the compound of the present invention can not generally be defined, as it varies depending upon the weather conditions, the type of the formulation, the application season, the application site or the types or degree of outbreak of the pest insects. However, it is usually applied in a concentration of the active ingredient being from 0.05 to 800,000 ppm, preferably from 0.5 to 500,000 ppm, and the dose per unit area is such that the compound of the present invention is from 0.05 to 10,000 g, preferably from 1 to 5,000 g, per hectare. The application of the insect pest control agent as a preferred embodiment of the pesticide containing the compound of the present invention, can not generally be defined, as it varies depending upon various conditions as mentioned above, but is usually carried out in a concentration of the active ingredient being from 0.1 to 500,000 ppm, preferably from 1 to 100,000 ppm, and the dose per unit area is such that the compound of the present invention is from 0.1 to 10,000 g, preferably from 10 to 1,000 g, per hectare. The application of the fungicide can not generally be defined, as it varies depending upon various conditions as described above, but is usually carried out in a concentration of the active ingredient being from 0.1 to 500,000 ppm, preferably from 1 to 100,000 ppm, and the dose per unit area is such that the compound of the present invention is from 0.1 to 10,000 g, preferably from 10 to 1,000 g, per hectare. Further, agricultural and horticultural pesticides as another preferred embodiment of pesticides containing the compounds of the present invention may be applied in accordance with the above-described application of insect pest control agents and fungicides. The present invention includes such a method for controlling insect pests by such applications.

Various formulations of pesticides such as insect pest control agents or fungicides containing the compounds of the present invention or their diluted compositions may be applied by conventional methods for application which are commonly employed, such as spraying (e.g. spraying, jetting, misting, atomizing, powder or grain scattering or dispersing in water), soil application (e.g. mixing or drenching), surface application (e.g. coating, powdering or covering) or impregnation to obtain poisonous feed. Further, it is possible to feed domestic animals with a food containing the above active ingredient and to control the outbreak or growth of pests, particularly insect pests, with their excrements. Furthermore, the active ingredient may also be applied by a so-called ultra low-volume application method. In this method, the composition may be composed of 100% of the active ingredient.

Further, the pesticides such as insect pest control agents or fungicides containing compounds of the present invention may be mixed with or may be used in combination with other agricultural chemicals, fertilizers or phytotoxicity-reducing agents, whereby synergistic effects or activities may sometimes be obtained. Such other agricultural chemicals include, for example, a herbicide, an insecticide, a miticide, a nematicide, a soil pesticide, a fungicide, an antivirus agent, an attractant, an antibiotic, a plant hormone and a plant growth regulating agent. Especially, with a mixed pesticide having a compound of the present invention mixed with or used in combination with one or more active compounds of other agricultural chemicals, the application range, the application time, the pesticidal activities, etc. may be improved to preferred directions. The compound of the present invention and the active compounds of other agricultural chemicals may separately be formulated so that they may be mixed for use at the time of application, or they may be formulated together. The present invention includes such a mixed pesticidal composition.

The mixing ratio of the compound of the present invention to the active compounds of other agricultural chemicals can not generally be defined, since it varies depending upon the weather conditions, the types of formulations, the application time, the application site, the types or degree of outbreak of insect pests, etc., but it is usually within a range of from 1:300 to 300:1, preferably from 1:100 to 100:1, by weight. Further, the dose for the application is such that the total amount of the active compounds is from 0.1 to 5,000 g, preferably from 10 to 3,000 g, per hectare. The present invention includes a method for controlling insect pests by an application of such a mixed pesticide composition.

The active compounds of insect pest control agents such as insecticides, miticides, nematicides or soil pesticides in the above-mentioned other agricultural chemicals, include, for example, (by common names, some of them are still in an application stage) organic phosphate compounds such as Profenofos, Dichlorvos, Fenamiphos, Fenitrothion, EPN, Diazinon, Chlorpyrifosmethyl, Acephate, Prothiofos, Fosthiazate, Phosphocarb, Cadusafos, and Disulfoton; carbamate compounds such as Carbaryl, Propoxur, Aldicarb, Carbofuran, Thiodicarb, Methomyl, Oxamyl, Ethiofencarb, Pirimicarb, Fenobucarb, Carbosulfan, and Benfuracarb; nereistoxin derivatives such as Cartap, and Thiocyclam; organic chlorine compounds such as Dicofol, and Tetradifon; organometallic compounds such as Fenbutatin Oxide; pyrethroid compounds such as Fenvalerate, Permethrin, Cypermethrin, Deltamethrin, Cyhalothrin, Tefluthrin, and Ethofenprox; benzoylurea compounds such as Diflubenzuron, Chlorfluazuron, Teflubenzuron, and Flufenoxuron; juvenile hormone-like compounds such as Methoprene; pyridazinone compounds such as Pyridaben; pyrazole compounds such as Fenpyroximate, Fipronil, Tebufenpyrad, Ethiprole, and Tolfenpyrad; neonicotinoids such as Imidacloprid, Nitenpyram, Acetamiprid, Thiacloprid, Thiamethoxam, Clothianidin, and Dinotefuran; hydrazine compounds such as Tebufenozide, Methoxyfenozide, and Chromafenozide; dinitro compounds; organic sulfur compounds; urea compounds; triazine compounds; hydrazone compounds; and other compounds, such as Buprofezin, Hexythiazox, Amitraz, Chlordimeform, Silafluofen, Triazamate, Pymetrozine, Pyrimidifen, Chlorfenapyr, Indoxacarb, Acequinocyl, Etoxazole, Cyromazin, and 1,3-dichloropropene. Further, BT agents, microbial agricultural chemicals such as insect viruses, or antibiotics such as Avermectin, Milbemycin and Spinosad, may be used in admixture or in combination.

The active compounds of fungicides among the above-mentioned other agricultural chemicals include, for example, (by common names, some of which are still in an application stage) pyrimidinamine compounds such as Mepanipyrim, Pyrimethanil, and Cyprodinil; azole compounds such as Triadimefon, Bitertanol, Triflumizole, Etaconazole, Propiconazole, Penconazole, Flusilazole, Myclobutanil, Cyproconazole, Terbuconazole, Hexaconazole, Furconazole-cis, Prochloraz, Metconazole, Epoxiconazole, Tetraconazole, Oxpoconazole, and Sipconazole; quinoxaline compounds such as Quinomethionate; dithiocarbamate compounds such as Maneb, Zineb, Mancozeb, Polycarbamate, Propineb; organic chlorine compounds such as Fthalide, Chlorothalonil, and Quintozene; imidazole compounds such as Benomyl, Thiophanate-Methyl, Carbendazim, and 4-chloro-2-cyano-1-dimethylsulfamoyl-5-(4-methylphenyl)imidazole; pyridinamine compounds such as Fluazinam; cyanoacetamide compounds such as Cymoxanil; phenylamide compounds such as Metalaxyl, Oxadixyl, Ofurace, Benalaxyl, Furalaxyl, and Cyprofuram; sulfenic acid compounds such as Dichlofluanid; copper compounds such as cupric hydroxide, and Oxine Copper; isoxazole compounds such as Hydroxyisoxazole; organophosphorus compounds such as Fosetyl-Al, Tolcofos-Methyl, S-benzyl O,O-diisopropylphosphorothioate, O-ethyl S,S-diphenylphosphorodithioate, and aluminumethylhydrogen phosphonate; N-halogenothioalkyl compounds such as Captan, Captafol, and Folpet; dicarboximide compounds such as Procymidone, Iprodione, and Vinclozolin; benzanilide compounds such as Flutolanil, Mepronil, and Zoxamide; piperazine compounds such as Triforine; pyrizine compounds such as Pyrifenox; carbinol compounds such as Fenarimol; and Flutriafol; piperidine compounds such as Fenpropidine; morpholine compounds such as Fenpropimorph; organotin compounds such as Fentin Hydroxide, and Fentin Acetate; urea compounds such as Pencycuron; cinnamic acid compounds such as Dimethomorph; phenylcarbamate compounds such as Diethofencarb; cyanopyrrole compounds such as Fludioxonil, and Fenpiclonil; Strobilurin compounds such as Azoxystrobin, Kresoxim-Methyl, Metominofen, Trifloxystrobin, and Picoxystrobin; oxazolidinedione compounds such as Famoxadone; thiazole carboxamide compounds such as Ethaboxam; Silyl amide compounds such as Silthiopham; aminoacid amidecarbamate compounds such as Iprovalicarb; imidazolidine compound such as Fenamidone; hydroxyanilide compounds such as Fenhexamid; benzene sulfonamide compounds such as Flusulfamide; anthraquinone compounds; crotonic acid compounds; antibiotics; and other compounds, such as Isoprothiolane, Tricyclazole, Pyroquilon, Diclomezine, Pro. benazole, Quinoxyfen, Propamocarb Hydrochloride, Spiroxamine, Chloropicrin, Dazomet, and Metam-Sodium.

Now, pesticides like marine antifouling agents will be described.

The marine antifouling agents containing the compounds of the present invention are effective for controlling noxious marine organisms against ships or underwater structures (such as harbour structures, buoys, pipelines, bridges, submarine bases, seabed oilfield drilling installations, water conduits for power plants, fixed shore nets and culturing nets). Specifically, they are effective for preventing the attachment and propagation of plants such as green algae and brown algae, animals such as a barnacle, a serpla, an ascidian, a sea mussel and an oyster, various bacteria called slime, and aquatics such as mold and a diatom, at the bottoms of ships or on underwater structures.

The marine antifouling agents containing the compounds of the present invention provide antifouling and antislime properties over a long period of time and exhibit excellent effects for preventing the attachment and propagation of noxious marine organisms against ships or underwater structures.

The marine antifouling agents containing the compounds of the present invention are usually formulated and used in the form of paint compositions. However, they may be formulated and used in other forms (such as solutions, emulsifiable concentrates, or pellets) as the case requires. Paint vehicles to be used for formulating the compounds of the present invention into coating compositions, may be resin vehicles which are commonly used. For example, a vinyl chloride resin, a vinyl chloride-vinyl acetate copolymer, a vinyl chloride-vinyl isobutyl ether copolymer, a chlorinated rubber resin, a chlorinated polyethylene resin, a chlorinated polypropylene resin, an acrylic resin, a styrene-butadiene resin, a polyester resin, an epoxy resin, a phenol resin, a synthetic rubber, a silicone rubber, a silicone resin, a petroleum resin, an oil and fat resin, a rosin ester resin, a rosin soap or rosin, may be mentioned. Further, as a vehicle having antifouling properties, an acrylic copolymer resin composition containing, as constituting units, an organotin compound salt of an unsaturated mono- or di-carboxylic acid, obtainable by a condensation reaction of (meth)acrylic acid with an organotin compound such as bis(tributyltin)oxide or triphenyltin hydroxide, or a resin containing a metal element such as copper, zinc or tellurium in its side chains, may, for example, be used.

When the compound of the present invention is formulated as a coating composition, the blend proportion is adjusted so that the compound of the present invention will be contained in an amount of from 0.1 to 60 wt %, preferably from 1 to 40 wt %, based on the entire coating composition.

The coating composition containing the compound of the present invention can be prepared by using e.g. a ball mill, a pebble mill, a roll mill or a sand grinder in accordance with a method which is well known in the field of preparing coating materials. Further, the above coating composition may contain a plasticizer, a coloring pigment, an extender pigment, an organic solvent, etc. which are commonly used in this field.

The coating composition containing the compound of the present invention may further contain any other known inorganic or organic antifouling agent, as the case requires. Such an antifouling agent includes, for example, cuprous oxide, copper rhodanide, copper hydroxide, copper naphthenate, metallic copper and various tin compounds and dithiocarbamic acid derivatives, such as tetramethylthiuram monosulfide, tetramethylthiuram disulfide, zinc bis-(dimethyldithiocarbamate), zinc ethylene-bis(dithiocarbamate), manganese ethylene-bis(dithiocarbamate), and copper bis(dimethyldithiocarbamate).

BEST MODE FOR CARRYING OUT THE INVENTION

Preferred embodiments of the present invention are as follows.

(1) A geometrical isomer which is the geometrical isomer of an acrylonitrile compound represented by the formula (I) or of its salt, wherein the geometrical isomer having a longer retention time when analyzed by reversed-phase liquid chromatography under the above-mentioned conditions, is an E-isomer.

(2) A geometrical isomer which is the geometrical isomer of an acrylonitrile compound represented by the formula (I) or of its salt, wherein the geometrical isomer having a longer retention time when analyzed by reversed-phase liquid chromatography under the above-mentioned conditions, is a Z-isomer.

(3) Among the geometrical isomer of an acrylonitrile compound represented by the formula (I) or of its salt, or a mixture thereof, the geometrical isomer mixture which contains at least 80% of the geometrical isomer having a longer retention time when analyzed by reversed-phase liquid chromatography under the above-mentioned conditions.

(4) Among the geometrical isomer of an acrylonitrile compound represented by the formula (I) or of its salt, or a mixture thereof, the geometrical isomer mixture which contains at least 90% of the geometrical isomer having a longer retention time when analyzed by reversed-phase liquid chromatography under the above-mentioned conditions.

(5) Among the geometrical isomer of an acrylonitrile compound represented by the formula (I) or of its salt, or a mixture thereof, the geometrical isomer mixture which contains at least 95% of the geometrical isomer having a longer retention time when analyzed by reversed-phase liquid chromatography under the above-mentioned conditions.

(6) A geometrical isomer or a geometrical isomer mixture containing such a geometrical isomer in a larger proportion produced by the method of the above reaction (A).

(7) A geometrical isomer or a geometrical isomer mixture containing such a geometrical isomer in a larger proportion produced by the method of the above reaction (B).

(8) A geometrical isomer or a geometrical isomer mixture containing such a geometrical isomer in a larger proportion produced by the method of the above reaction (C).

(9) A process in which in the above reaction (A), as the base, an alkali metal carbonate or a tertiary amine is used, and as the solvent, a polar aprotic solvent or a ketone is used.

(10) A process wherein in the above reaction (A), as the base, sodium carbonate, potassium carbonate or 1,8-diazabicyclo[5.4.0]-7-undecene is used, and as the solvent, dimethylformamide, acetonitrile, acetone or methyl ethyl ketone is used.

(11) A process wherein in the above reaction (A), as the base, an alkali metal carbonate is used, and as the solvent, a polar aprotic solvent or a ketone is used.

(12) A process wherein in the above reaction (A), as the base, sodium carbonate or potassium carbonate is used, and as the solvent, dimethylformamide, acetonitrile, acetone or methyl ethyl ketone, is used.

(13) A geometrical isomer or a geometrical isomer mixture containing such geometrical isomer in a larger proportion, which is produced by the process of the above (9), (10), (11) or (12).

(14) A process wherein in the above reaction (B), as the solvent, a non-polar solvent is used under irradiation with ultraviolet rays.

(15) A process wherein in the above reaction (B), as the solvent, an aromatic hydrocarbon or an aliphatic hydrocarbon is used under irradiation with ultraviolet rays.

(16) A process wherein in the above reaction (B), as the solvent, benzene, toluene or hexane is used under irradiation with ultraviolet rays.

(17) A process wherein in the above reaction (B), as the light source, a sunbeam or a mercury lamp is used, and as the solvent, benzene, toluene or hexane is used.

(18) A geometrical isomer or a geometrical isomer mixture containing such geometrical isomer in a larger proportion, which is produced by the process of the above (14), (15), (16) or (17).
(19) A process wherein in the above reaction (C), as the base, a strong base is used, and as the solvent, an aromatic hydrocarbon, an ether or a polar aprotic solvent is used.
(20) A process wherein in the above reaction (C), as the base, an alkali metal hydride or an organic lithium is used, and as the solvent, an ether or a polar aprotic solvent such as dimethylacetamide or dimethylformamide, is used.
(21) A process wherein in the above reaction (C), as the base, sodium hydride, potassium hydride methyl lithium, n-butyl lithium, tert-butyl lithium or phenyl lithium is used, and as the solvent, dioxane, tetrahydrofuran, diethyl ether, dimethylacetamide or dimethylformamide is used.
(22) A process wherein in the above reaction (C), as the base, an alkali metal hydride is used, and as the solvent, an ether or a polar aprotic solvent such as dimethylacetamide or dimethylformamide, is used.
(23) A process wherein in the above reaction (C), as the base, sodium hydride or potassium hydride is used, and as the solvent, tetrahydrofuran or dimethylformamide is used.
(24) A geometrical isomer or a geometrical isomer mixture containing such geometrical isomer in a larger proportion, which is produced by the process of the above (19), (20), (21), (22) or (23).
(25) The geometrical isomer of an acrylonitrile compound represented by the formula (I), which is an E-isomer, or its salt.
(26) The geometrical isomer of an acrylonitrile compound represented by the formula (I), which is a Z-isomer, or its salt.
(27) The above (1) to (26) wherein $R_1$ in the above formula (I) is —C(=O)$R_4$.
(28) The above (1) to (26) wherein $R_1$ in the above formula (I) is —C(=S)$R_4$.
(29) A pesticide containing the geometrical isomer or the geometrical isomer mixture containing such geometrical isomer in a larger proportion, of the above (1) to (28) as an active ingredient.
(30) An insecticide, miticide or nematicide containing the geometrical isomer or the geometrical isomer mixture containing such geometrical isomer in a larger proportion, of the above (1) to (28) as an active ingredient. (31) A method for controlling a pest, which comprises applying the geometrical isomer or the geometrical isomer mixture containing such geometrical isomer in a larger proportion, of the above (1) to (28) as an active ingredient, to the pest.

EXAMPLES

Now, Examples of the present invention will be described, but the present invention is by no means limited thereto. In each Preparation Example, the isomer ratio is a ratio of the geometrical isomer having a shorter retention time:the geometrical isomer having a longer retention time when analyzed by the above-mentioned reversed-phase liquid chromatography [peak area ratio by HPLC (reversed-phase liquid chromatography) ultraviolet absorption detector].

Preparation Example 1

Preparation of α-(4-tert-Butylphenyl)-β-[(ethylthio)carbonyloxy]-β-(2-trifluoromethylphenyl) acrylonitrile (Isomer Ratio 2:98, Compound A)

A mixture comprising 2.0 g of 4-tert-butylbenzyl cyanide, 2.34 g of 2-trifluoromethylbenzoyl chloride and 8 ml of dimethylformamide, was dropwise added to a mixture comprising 0.83 g of 68% sodium hydride and 13 ml of dimethylformamide, while maintaining the temperature at 40° C. After completion of the dropwise addition, the reaction was carried out at room temperature for 30 minutes. The reaction mixture was cooled with ice, and a mixture comprising 1.77 g of ethyl chlorothiolformate and 1.2 ml of dimethylformamide, was dropwise added. After completion of the dropwise addition, the reaction was carried out for 30 minutes under cooling with ice. The reaction mixture was poured into ice water and extracted with methylene chloride, followed by washing with water. The organic layer was dried over anhydrous sodium sulfate and concentrated under reduced pressure. The residue was purified by silica gel column chromatography (eluting solvent: ethyl acetate/n-hexane=1/9) to obtain 3.9 g of a desired product (isomer ratio 2:98) having a melting point of 116 to 117° C. The HPLC conditions for the analysis of this product and the NMR spectrum data of this product are as follows.

HPLC conditions

Stationary phase: Octadecyl group-type column (Wakosil-II5C18), 4.6 mm×250 mm: manufactured by Wako Pure Chemical Industries, Ltd.

Mobile phase: Acetonitrile/water=4/1 (V/V)

Detection wavelength: 254 nm

Column temperature: 40° C.

Flow rate: 1 ml/min $^1$H-NMR δ ppm (Solvent:CDCl$_3$/400 MHz) 1.17 (t, 3H), 1.31 (s, 9H), 2.75 (q, 2H), 7.46 (d, 2H), 7.58 (d, 2H), 7.61 (t, 1H), 7.68 (t, 1H), 7.77 (d, 1H), 7.83 (d, 1H).

Preparation Example 2

Preparation of α-(4-tert-Butylphenyl)-β-[(n-propyloxy)carbonyloxy]-β-(2-trifluoromethylphenyl) acrylonitrile (Isomer Ratio 7:93, Compound B)

A mixture comprising 2.0 g of 4-tert-butylbenzyl cyanide, 2.35 g of 2-trifluoromethylbenzoyl chloride and 8 ml of dimethylformamide, was dropwise added to a mixture comprising 0.84 g of 68% sodium hydride and 13 ml of dimethylformamide while maintaining the temperature at a level of from 40 to 50° C. After completion of the dropwise addition, the reaction was carried out for 30 minutes at room temperature. The reaction mixture was cooled with ice, and a mixture comprising 1.5 g of n-propyl chloroformate and 1.2 ml of dimethylformamide, was dropwise added. After completion of the dropwise addition, the reaction was carried out for 30 minutes under cooling with ice. The reaction mixture was poured into ice water and extracted with methylene chloride and then washed with water. The organic layer was dried over anhydrous sodium sulfate and concentrated under reduced pressure. The residue was purified by silica gel column chromatography (eluting solvent: ethyl acetate/n-hexane=1/9) to obtain 3.4 g of the desired product (isomer ratio 7:93) having a melting point of 44 to 45° C. The HPLC conditions for the analysis of this product were the same as in Preparation Example 1. Further, the NMR spectrum data of this product are as follows.

$^1$H-NMR δ ppm (Solvent:CDCl$_3$/400 MHz) 0.84 (t, 3H), 1.33 (s, 9H), 1.57 (m, 2H), 4.01 (t, 2H), 7.45 (d, 2H), 7.61 (d, 2H), 7.64 (t, 1H), 7.68 (t, 1H), 7.77 (d, 1H), 7.86 (d, 1H).

Preparation Example 3

Preparation of α-(4-tert-Butylphenyl)-β-[ethoxy(thiocarbonyl)oxy]-β-(2-trifluoromethylphenyl) acrylonitrile (Isomer Ratio 35:65, Compound C)

A mixture comprising 2.0 g of 4-tert-butylbenzyl cyanide, 2.34 g of 2-trifluoromethylbenzoyl chloride and 8 ml of dimethylformamide, was dropwise added to a mixture comprising 0.83 g of 68% sodium hydride and 13 ml of dimethylformamide while maintaining the temperature at a level of from 40 to 500C. After completion of the dropwise addition, the reaction was carried out for 30 minutes at room temperature. The reaction mixture was cooled with ice, and a mixture comprising 2.1 g of ethyl chlorothioformate and 1.2 ml of dimethylformamide, was dropwise added. After completion of the dropwise addition, the reaction was carried out for 30 minutes under cooling with ice. The reaction mixture was poured into ice water and extracted with methylene chloride and then washed with water. The organic layer was dried over anhydrous sodium sulfate and concentrated under reduced pressure. The residue was purified by silica gel column chromatography (eluting solvent: ethyl acetate/n-hexane=1/9) to obtain 3.2 g of the desired product (isomer ratio 35:65) having a melting point of 62 to 64° C. The HPLC conditions for the analysis of this product were the same as in Preparation Example 1. Further, the NMR spectrum data of the respective geometrical isomers are as follows.

$^1$H-NMR δ ppm (Solvent:CDCl$_3$/400 MHz); The geometrical isomer having a shorter retention time: 1.23 (s, 9H), 1.40 (t, 3H), 4.49 (q, 2H), 7.07 (d, 2H), 7.22 (d, 2H), 7.37 (d, 1H), 7.47 (t, 1H), 7.57 (t,$_1$H), 7.73 (d, 1H); The geometrical isomer having a longer retention time: 1.27 (t, 3H), 1.35 (s, 9H), 4.39 (q, 2H), 7.44 (d, 2H), 7.58 (d, 2H), 7.60 (t, 1H), 7.66 (t, 1H), 7.76 (d, 1H), 8.02 (d, 1H).

Preparation Example 4

Preparation of α-(4-tert-Butylphenyl)-β-[(methylthio)carbonyloxy]-β-(2-trifluoromethylphenyl)acrylonitrile (Isomer Ratio 14:86, Compound D)

1.14 g of triethylamine was added to a mixture comprising 3.0 g of α-(4-tert-butylphenyl)-β-hydroxy-β-(2-trifluoromethylphenyl)acrylonitrile and 25 ml of dichloroethane, and a mixture comprising 1.19 g of methyl chlorothiolformate and 5 ml of dichloroethane, was added thereto under cooling with ice. After completion of the dropwise addition, the reaction was carried out for 15 minutes under cooling with ice. The reaction mixture was washed with water and dried over anhydrous sodium sulfate, and then concentrated under reduced pressure. The residue was purified by silica gel column chromatography (eluting solvent: ethyl acetate/n-hexane=1/9), and the obtained solid was washed with n-hexane to obtain 3.0 g of the desired product (isomer ratio 14:86) having a melting point of 92 to 102° C. The HPLC conditions for the analysis of this product were the same as in Preparation Example 1. Further, the NMR spectrum data of the respective geometrical isomers are as follows.

$^1$H-NMR δ ppm (Solvent:CDCl$_3$/400 MHz); The geometrical isomer having a shorter retention time: 1.22 (s, 9H), 2.34 (s, 3H), 7.02 (d, 2H), 7.19 (d, 2H), 7.33 (d, 1H), 7.42 (t, 1H), 7.51 (t, 1H), 7.75 (d, 1H); The geometrical isomer having a longer retention time: 1.33 (s, 9H), 2.25 (s, 3H), 7.46 (d, 2H), 7.57 (d, 2H), 7.59 (t, 1H), 7.63 (t, 1H), 7.77 (d, 1H), 7.84 (d, 1H).

Preparation Example 5

Preparation of α-(4-tert-Butylphenyl)-β-[(methylthio)carbonyloxy]-β-(2-trifluoromethylphenyl)acrylonitrile (Isomer Ratio 2:98, Compound E)

A mixture comprising 5.0 g of α-(4-tert-butylphenyl)-β-hydroxy-β-(2-trifluoromethylphenyl)acrylonitrile, 1.5 g of sodium carbonate and 30 ml of methyl ethyl ketone, was heated to 70° C., and a mixture comprising 2.1 g of methyl chlorothiolformate and 10 ml of methyl ethyl ketone, was dropwise added over a period of 10 minutes. After completion of the dropwise addition, the reaction was carried out for 30 minutes at a temperature of from 70 to 75° C. The reaction mixture was cooled, and then an inorganic salt was filtered off. The cake was washed with 20 ml of methyl ethyl ketone. Methyl ethyl ketone in the filtrate was distilled off, and to the residue, 50 ml of an isoparaffin type hydrocarbon (tradename: ISOPAR G, manufactured by EXXON CHEMICAL) was added, followed by heating for dissolution, and the solution was left to cool to room temperature. Precipitated crystals were collected by filtration, and the cake was washed with 10 ml of ISOPAR G (tradename) and then dried at 65° C. for 12 hours to obtain 4.9 g of the desired product (isomer ratio 2:98). The HPLC conditions for the analysis of this product were as follows. Further, the NMR spectrum data of this product were the same as in Preparation Example 4.

HPLC conditions

Stationary phase: Octadecyl group-type column (tradename: COSMOSIL 5C18-AR-II) 4.6 mm×250 mm; manufactured by Nacalai Tesque, Inc.

Mobile phase: Acetonitrile/1% H$_3$PO$_4$ aqueous solution= 4/1 (V/V)

Detection wavelength: 254 nm

Column temperature: 40° C.

Flow rate: 1 ml/min

Preparation Example 6

Preparation of α-(4-tert-Butylphenyl)-β-[(methylthio)carbonyloxy]-β-(2-trifluoromethylphenyl)acrylonitrile (Isomer Ratio 0:100, Compound F)

A mixture comprising 5.0 g of α-(4-tert-butylphenyl)-β-hydroxy-β-(2-trifluoromethylphenyl)acrylonitrile, 2.0 g of sodium carbonate and 30 ml of acetone, was heated, and a mixture comprising 2.1 g of methyl chlorothiolformate and 10 ml of acetone, was dropwise added over a period of 10 minutes under reflux. After completion of the dropwise addition, the reaction was carried out for 60 minutes under reflux. The reaction mixture was cooled, and then, an inorganic salt was filtered off. The cake was washed with 20 ml of acetone. Acetone in the filtrate was distilled off, and 50 ml of ISOPAR G (tradename) was added to the residue, followed by heating and dissolution. Then, the solution was left to cool to room temperature. Precipitated crystals were collected by filtration, and the cake was washed with 10 ml of ISOPAR G (tradename) and then dried at 45° C. for 12 hours to obtain 4.8 g of the desired product (isomer ratio 0:100). The HPLC conditions for the analysis of this product were the same as in Preparation Example 5. Further, the NMR spectrum data of this product were the same as the geometrical isomer having a longer retention time of Preparation Example 4.

Preparation Example 7

Preparation of α-(4-Chlorophenyl)-β-(S-methyldithiocarbonyloxy)-β-(2-trifluoromethylphenyl)acrylonitrile (Isomer Ratio 25:75, Compound G)

1) A mixture comprising 4 g of 68% sodium hydride and 150 ml of dimethylformamide was heated to a temperature of from 50 to 60° C., and a mixed solution comprising 33 g of α-(4-chlorophenyl)-β-hydroxy-β-(2-trifluoromethylphenyl)acrylonitrile and 70 ml of dimethylformamide, was dropwise added thereto over a period of 1 hour at a temperature of from 55 to 65° C. After completion of the dropwise addition, the reaction was carried out for 30 minutes at the same temperature, and the solution temperature was returned to room temperature. Then, 12.9 g of methyl chlorodithioformate was dropwise added over a period of 15 minutes at 25° C. After completion of the dropwise addition, the reaction was carried out for 1.5 hours. The reaction mixture was poured into 500 ml of ice water and extracted twice with 300 ml of ether. The organic layer was washed with water and a saturated sodium chloride aqueous solution and dried over anhydrous magnesium sulfate. 120 ml of n-pentane was added to the residue obtained by concentration under reduced pressure, followed by heating and stirring. Further, stirring was carried out under cooling with ice for 1 hour for crystallization, and a colored component was removed to obtain 34.6 g of α-(4-chlorophenyl)-β-(S-methyldithiocarbonyloxy)-β-(2-trifluoromethylphenyl)acrylonitrile (isomer ratio 55:45, compound H) having a melting point of 80.8° C. The HPLC conditions for the analysis of this product were as follows.

HPLC conditions

Solid phase: Octadecyl group-type column (tradename: COSMOSIL 5C18) 4.6 mm×150 mm; manufactured by Nacalai Tesque, Inc.

Mobile phase: Acetonitrile/water =3/1 (V/V)

Detection wavelength: 254 nm

Column temperature: 40° C.

Flow rate: 1 ml/min

2) A solution obtained by dissolving 20 g of α-(4-chlorophenyl)-β-(S-methyldithiocarbonyloxy)-β-(2-trifluoromethylphenyl)acrylonitrile having an isomer ratio of 55:45 in 1.2 l of benzene, was irradiated for 2.5 hours with a high pressure mercury lamp (450 W) at room temperature under a nitrogen gas atmosphere. After completion of the irradiation, concentration under reduced pressure was carried out, and the residue was purified by silica gel column chromatography (eluting solvent: ethyl acetate/n-hexane=1/9) to obtain 17 g of the desired product (isomer ratio 25:75) having a melting point of 79.5° C. The HPLC conditions for the analysis of this product were the same as in the above step 1). Further, the NMR spectrum data of the respective isomers are as follows.

$^1$H-NMR δ ppm (Solvent:CDCl$_3$/400 MHz); The geometrical isomer having a shorter retention time: 2.58 (s, 3H), 7.06 (d, 2H), 7.15 (d, 2H), 7.32 (m, 2H), 7.51 (m, 1H), 7.74 (m, 1H); The geometrical isomer having a longer retention time: 2.47 (s, 3H), 7.42 (d, 2H), 7.54 (d, 2H), 7.63 (m, 2H), 7.75 (m, 1H), 7.98 (m, 1H).

Preparation Example 8

Preparation of α-(4-Chlorophenyl)-β-(S-ethyldithiocarbonyloxy)-β-(2-trifluoromethylphenyl) acrylonitrile (Isomer Ratio 28:72, Compound I)

1) A mixed solution comprising 500 mg of α-(4-chlorophenyl)-β-hydroxy-β-(2-trifluoromethylphenyl)acrylonitrile and 2 ml of dimethylformamide, was gradually dropwise added under cooling with ice to a mixture comprising 68 mg of 60% sodium hydride and 10 ml of dimethylformamide. After completion of the dropwise addition, the temperature was gradually returned to room temperature, and stirring was continued until generation of hydrogen gas terminated. Thereafter, the mixture was again cooled with ice, and a mixed solution comprising 240 mg of ethyl chlorodithioformate and 2 ml of dimethylformamide, was gradually dropwise added. After completion of the dropwise addition, the reaction was carried out for 2 hours at room temperature. The reaction mixture was poured into 100 ml of ice water and extracted by an addition of 150 ml of ether. The organic layer was washed with water and a saturated sodium chloride aqueous solution and dried over anhydrous magnesium sulfate. The solvent was distilled off. The residue was purified by silica gel column chromatography (eluting solvent: ethyl acetate/n-hexane=1/9) to obtain 380 mg of α-(4-chlorophenyl)-β-(S-ethyldithiocarbonyloxy)-β-(2-trifluoromethylphenyl) acrylonitrile (isomer ratio 52:48, compound J) having a refractive index $n_D^{27.2}$ of 1.5612. The HPLC conditions for the analysis of this product were the same as in Preparation Example 7.

2) A solution obtained by dissolving 2 g of α-(4-chlorophenyl)-β-(S-ethyldithiocarbonyloxy)-β-(2-trifluoromethylphenyl)acrylonitrile having an isomer ratio of 52:48 in 100 ml of benzene, was irradiated for 4 hours with a high pressure mercury lamp (100 W) at room temperature under a nitrogen gas atmosphere. After completion of the irradiation, the solvent was distilled off, and the residue was purified by silica gel column chromatography (eluting solvent: ethyl acetate/n-hexane=1/9) to obtain 1.8 g of the desired product (isomer ratio 28:72) having a melting point of 81.7° C. The HPLC conditions for the analysis of this product were the same as in Preparation Example 7. Further, the NMR spectrum data of the respective isomers are as follows.

$^1$H-NMR δ ppm (Solvent:CDCl$_3$/400 MHz); The geometrical isomer having a shorter retention time: 1.23 (t, 3H), 3.01 (q, 2H), 7.44 (d, 2H), 7.56 (d, 2H), 7.65 (m, 2H), 7.77 (m, 1H), 7.97 (m, 1H); The geometrical isomer having a longer retention time: 1.35 (t, 3H), 3.14 (q, 2H), 7.07 (d, 2H), 7.19 (d, 2H), 7.29 (m, 2H), 7.49 (m, 1H), 7.74 (m, 1H).

Preparation Example 9

Preparation of α-(4-Chlorophenyl)-β-(S-methyldithiocarbonyloxy)-β-(2-trifluoromethylphenyl)acrylonitrile (Isomer Ratio 0:100, Compound K)

A solution obtained by dissolving 0.34 g of methyl chlorodithioformate in 2 ml of dimethylformamide, was dropwise added at room temperature to a solution obtained by dissolving 0.8 g of α-(4-chlorophenyl)-β-hydroxy-β-(2-trifluoromethylphenyl)acrylonitrile and 0.41 g of 1,8-diazabicyclo[5.4.0]-7-undecene in 10 ml of dimethylformamide. After completion of the dropwise addition, the reaction was carried out for 8 hours at room temperature. The reaction mixture was poured into 50 ml of ice water and extracted by an addition of 100 ml of ether. The organic layer was washed with water and a saturated sodium chloride aqueous solution and dried over anhydrous magnesium sulfate, and the solvent was distilled off. The residue was purified by silica gel column chromatography (eluting solvent: ethyl acetate/n-hexane=1/9) to obtain 0.2 g of the desired product (isomer ratio 0:100) having a melting point of 91.7° C. The HPLC conditions for the analysis of this product were the same as in Preparation Example 7. Further, the NMR spectrum data of this product are the same as the geometrical isomer having a longer retention time in Preparation Example 7.

Reference Preparation Example 1

Preparation of α-(4-tert-Butylphenyl)-β-hydroxy-β-(2-trifluoromethylphenyl)acrylonitrile A mixture comprising 5.8 g of 63% sodium hydride and 137 ml of tetrahydrofuran was heated, and a mixture comprising 13.5 g of 4-tert-butylbenzyl cyanide, 15.0 g of 2-trifluoromethylbenzoyl chloride and 50 ml of tetrahydrofuran, was dropwise added thereto over a period of 2 hours under reflux. After completion of the dropwise addition, the reaction was carried out at the same temperature for 2 hours. Tetrahydrofuran in the reaction mixture was distilled off, and 250 ml of water was poured into the residue. Then, 80 ml of n-hexane was added thereto, and the mixture was stirred and washed for 10 minutes and then left to stand for 30 minutes. Then, the aqueous layer was separated. To the aqueous layer, 8.3 g of concentrated hydrochloric acid was gradually dropwise added with stirring, followed by further stirring for 30 minutes. Precipitated crystals were collected by filtration and washed with 100 ml of water and then dried at 55° C. for 24 hours to obtain 23.7 g of the desired product. The NMR spectrum data of this product were as follows.

$^1$H-NMR δ ppm (Solvent:CDCl$_3$/400 MHz) 1.36 (S, 9H), 6.42 (S, 1H), 7.52 (d, 2H), 7.57 (d, 2H), 7.62–7.69 (m, 3H), 7.79 (d, 1H)

Reference Preparation Example 2

Preparation of α-(4-tert-Butylphenyl)-β-hydroxy-β-(2-trifluoromethylphenyl)acrylonitrile A mixture comprising 5.8 g of 63% sodium hydride, 25 ml of tetrahydrofuran and 10 ml of liquid paraffin, was heated, and a mixture comprising 13.5 g of 4-tert-butylbenzyl cyanide and 15.0 g of 2-trifluoromethylbenzoyl chloride, was dropwise added thereto over a period of 2 hours at a temperature of from 65 to 70° C. After completion of the dropwise addition, the reaction was carried out for 2 hours at the same temperature. The reaction mixture was left to cool to room temperature, and 250 ml of water was poured into the solution. Then, 80 ml of n-hexane was poured, followed by stirring and washing for 10 minutes, and the mixture was left to stand still for 30 minutes, whereupon the aqueous layer was separated and obtained. To the aqueous layer, 8.3 g of concentrated hydrochloric acid was gradually dropwise added with stirring, followed by further stirring for 30 minutes. Precipitated crystals were collected by filtration and washed with 100 ml of water, and then dried at 55° C. for 24 hours to obtain 23.8 g of the desired product. The NMR spectrum data of this product were the same as in Reference Preparation Example 1.

Reference Preparation Example 3

Preparation of α-(4-Chlorophenyl)-β-hydroxy-β-(2-trifluoromethylphenyl)acrylonitrile A mixture comprising 45 g of 4-chlorobenzyl cyanide, 62 g of 2-trifluoromethylbenzoyl chloride and 210 ml of tetrahydrofuran, was dropwise added over a period of 1 hour at a temperature of not higher than 15° C. to the mixture comprising 70 g of potassium tertiary butyrate and 450 ml of tetrahydrofuran. After completion of the dropwise addition, the solution temperature was returned to room temperature, followed by the reaction for 1 hour. 500 ml of ice water was poured into the residue obtained by concentration under reduced pressure of the reaction mixture, followed by stirring for 15 minutes, whereupon the mixture was washed with 500 ml of methylene chloride. The aqueous layer was adjusted to pH 3 to 4 by concentrated hydrochloric acid and then extracted with 600 ml of methylene chloride. The organic layer was dried over anhydrous magnesium sulfate and concentrated under reduced pressure. 300 ml of n-hexane was added to the residue, followed by washing to obtain 87.6 g of the desired product. The NMR spectrum data of this product are as follows.

$^1$H-NMR δ ppm (Solvent:CDCl$_3$/400 MHz) 7.41 (d, 2H), 7.58–7.68 (m, 5H), 7.75 (m, 1H)

Reference Preparation Example 4

Preparation of α-(4-Chlorophenyl)-β-hydroxy-β-(2-trifluoromethylphenyl)acrylonitrile 5.8 g of 4-chlorobenzyl cyanide, 10 g of ethyl 2-trifluoromethylbenzoate and 2.9 g of sodium ethylate were added to 100 ml of toluene and then reacted for 8 hours under reflux. The reaction mixture was returned to room temperature and extracted by an addition of 200 ml of water. The aqueous phase was adjusted to pH 6 to 7 with 6N hydrochloric acid and then extracted by an addition of 400 ml of methylene chloride. The organic layer was washed with water and a saturated sodium chloride aqueous solution and dried over anhydrous magnesium sulfate. The solvent was distilled off under reduced pressure to obtain 6.3 g of the desired product. The NMR spectrum data of this product were the same as in Reference Preparation Example 3.

Now, Test Examples of the present invention will be described.

Test Example 1

A 10% water-based suspension concentrate of each of compound D and compound E was dispersed in water to obtain a chemical solution wherein the active ingredient is 150 ppm. Such a chemical solution was applied to satsuma mandarin (*Citrus unshiu* Marc.) infested with citrus red mite (*Panonychus citri*) (planted in a plastic pot having a diameter of 24 cm and a height of 29 cm) by means of a sprayer and then left to stand in a greenhouse. Before the application and on the 7th day, 12th day, 18th day and 26th day after the application, the number of adult citrus red mite on all leaves of the satsuma mandarin tree was counted. The results are shown in Table 1.

TABLE 1

| | Number of adult citrus red mite | | | | |
|---|---|---|---|---|---|
| Compound | Before application | 7th day | 12th day | 18th day | 26th day |
| D | 111 | 0 | 4 | 2 | 65 |
| E | 106 | 0 | 2 | 1 | 4 |
| Untreated | 63 | 86 | 65 | 87 | 363 |

It is evident from Table 1 that both compound D and E show excellent pesticidal effects, and that compound E shows superior pesticidal effects.

Test Example 2

A 10% water-based suspension concentrate of each of compounds H and G was dispersed in water containing 0.02% of a spreader (Shinrino, manufactured by NIHON NOHYAKU CO., LTD.) to obtain a chemical solution wherein the active ingredient was 150 ppm. Such a chemical solution was applied to an eggplant (*Solanum melongena*) infested with two-spotted spider mite (*Tetranychus urticae*) (planted in a plastic pot having a diameter of 17 cm and a height of 19 cm) by means of a sprayer, and then left to stand in a greenhouse. Before the application and on the 5th day, 9th day, 12th day and 15th day after the application, the number of adult two-spotted spider mite on the eggplant was counted. The results are shown in Table 2.

TABLE 2

| | Number of adult two-spotted spite mite | | | | |
|---|---|---|---|---|---|
| Compound | Before application | 5th day | 9th day | 12th day | 15th day |
| H | 111 | 0 | 1 | 18 | 42 |
| G | 106 | 1 | 0 | 2 | 4 |
| Untreated | 97 | 218 | 218 | 420 | 365 |

It is evident from Table 2 that both compound H and compound G show excellent pesticidal effects and that compound G shows superior pesticidal effects.

What is claimed is:

1. A geometrical isomer of an acrylonitrile compound represented by formula (I) or a salt thereof:

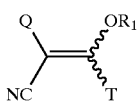

(I)

wherein T is phenyl which is substituted by $R_2$, or pyridyl which is substituted by $R_2$, Q is phenyl which may be substituted by $R_3$, thienyl which may be substituted by $R_3$, pyridyl which may be substituted by $R_3$, or benzyl which may be substituted by $R_3$, $R_1$ is —C(=O)$R_4$ or —C(=S)$R_4$, each of $R_2$ and $R_3$ is halogen, alkyl which may be substituted, alkenyl which may be substituted, alkynyl which may be substituted, alkoxy which may be substituted, alkenyloxy which may be substituted, alkynyloxy which may be substituted, alkythio which may be substituted, alkylsulfinyl which may be substituted, alkylsulfonyl which may be substituted, alkenylthio which may be substituted, alkenylsufinyl which may be substituted, alkenylsulfonyl which may be substituted, alkynylthio which may be substituted, alkynylsulfinyl which may be substituted, alkynylsulfonyl which may be substituted, nitro, cyano, phenyl which may be substituted, phenoxy which may be substituted, phenylthio which may be substituted, phenylsulfinyl which may be substituted, phenylsulfonyl which may be substituted, benzyl which may be substituted, benzyloxy which may be substituted, benzylthio which may be substituted, or benzoyl which may be substituted, $R_4$ is alkyl which may be substituted, alkenyl which may be substituted, alkynyl which may be substituted, alkoxy which may be substituted, alkenyloxy which may be substituted, alkynyloxy which may be substituted, alkylthio which may be substituted, alkenylthio which may be substituted, alkynylthio which may be substituted, cycloalkyl, cycloalkyloxy, cycloalkythio —N($R_5$)$R_6$, phenyl which may be substituted, phenoxy which may be substituted, phenylthio which may be substituted, benzyl which may be substituted, benzyloxy which may be substituted, benzylthio which may be substituted, each of $R_5$ and $R_6$ is hydrogen, alkyl or alkoxy, excluding (1) a compound wherein T is phenyl which is substituted by $R_2$, Q is thienyl which may be substituted by $R_3$, $R_1$ is —C(=O)$R_4$, and $R_4$ is alkyl which may be substituted, alkenyl which may be substituted, alkynyl which may be substituted, alkoxy which may be substituted, alkenyloxy which may be substituted, alkynyloxy which may be substituted, cycloalkyl, cycloalkyloxy, —N($R_5$)$R_6$, phenyl which may be substituted, phenoxy which may be substituted, phe-nylthio which may be substituted, benzyl which may be substituted, benzyloxy which may be substituted, benzylthio which may be substituted, (2) a compound wherein T is phenyl which is substituted by $R_2$, Q is thienyl which may be substituted by $R_3$, $R_1$ is —C(=S)$R_4$, and $R_4$ is —N($R_5$)$R_6$, (3) a compound wherein T is pyridyl which is substituted by $R_2$, Q is thienyl which may be substituted by $R_3$, or pyridyl which may be substituted by $R_3$, $R_1$ is —C(=O)$R_4$, and $R_4$ is alkyl, (4) α-(3,5-dimethoxyphenyl)-β-(2-methoxy-4-methylphenyl)-β-acetoxyacrylonitrile, and (5) α-(3,5-dimethoxyphenyl)-β-(2,6-dimethoxy-4-methylphenyl)-β-acetoxyacrylonitrile, wherein a geometrical isomer has a longer retention time when analyzed by reversed-phase liquid chromatography in which a packing comprising silica having chemically bonded thereto an alkyl group selected from trimethyl, octyl and octadecyl, is used as the stationary phase and a polar solvent selected from water, methanol and acetonitrile is used as a mobile phase, and the geometrical isomer mixture contains at least 60% of the geometrical isomer having a longer retention time.

2. The geometrical isomer mixture according to claim 1, wherein the geometrical isomer having a longer retention time is an E-isomer.

3. The geometrical isomer mixture according to claim 1, wherein the geometrical isomer having a longer retention time is a Z-isomer.

4. A geometrical isomer of an acrylonitrile compound represented by the formula (I) or a salt thereof:

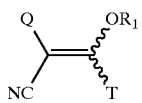

(I)

wherein T is phenyl which is substituted by $R_2$, or pyridyl which is substituted by $R_2$, Q is phenyl which may be substituted by $R_3$, thienyl which may be substituted by $R_3$, pyridyl which may be substituted by $R_3$, or benzyl which may be substituted by $R_3$, $R_1$ is —C(=O)$R_4$ or —C(=S)$R_4$, each of $R_2$ and $R_3$ is halogen, alkyl which may be substituted, alkenyl which may be substituted, alkynyl which may be substituted, alkoxy which may be substituted, alkenyloxy which may be substituted, alkynyloxy which may be substituted, alkythio which may be substituted, alkylsulfinyl which may be substituted, alkylsulfonyl which may be substituted, alkenylthio which may be substituted, alkenylsufinyl which may be substituted, alkenylsulfonyl which may be substituted, alkynylthio which may be substituted, alkynylsulfinyl which may be substituted, alkynylsulfonyl which may be substituted, nitro, cyano, phenyl which may be substituted, phenoxy which may be substituted, phenylthio which may be substituted, phenylsulfinyl which may be substituted, phenylsulfonyl which may be substituted, benzyl which may be substituted, benzyloxy which may be substituted, benzylthio which may be substituted, or benzoyl which may be substituted, $R_4$ is alkyl which may be substituted, alkenyl which may be substituted, alkynyl which may be substituted, alkoxy which may be substituted, alkenyloxy which may be substituted, alkynyloxy which may be substituted, alkylthio which may be substituted, alkenylthio which may be substituted, alkynylthio which may be substituted, cycloalkyl, cycloalkyloxy, cycloalkythio —N($R_5$)$R_6$, phenyl which may be substituted, phenoxy which may be substituted, phenylthio which may be substituted, benzyl which may be substituted, benzyloxy which may be substituted, benzylthio which may be substituted, each of $R_5$ and $R_6$ is hydrogen, alkyl or alkoxy, excluding (1) a compound wherein T is phenyl which is substituted by $R_2$, Q is thienyl which may be substituted by $R_3$, $R_1$ is —C(=O)$R_4$, and $R_4$ is alkyl which may be substituted, alkenyl which may be substituted, alkynyl which may be substituted, alkoxy which may be substituted, alkenyloxy which may be substituted, alkynyloxy which may be substituted, cycloalkyl, cycloalkyloxy, —N($R_5$)$R_6$, phenyl which may be substituted, phenoxy which may be substituted, phenylthio which may be substituted, benzyl which may be substituted, benzyloxy which may be substituted, benzylthio which may be substituted, (2) a compound wherein T is phenyl which is substituted by $R_2$, Q is thienyl which may be substituted by $R_3$, $R_1$ is —C(=S)$R_4$, and $R_4$ is —N($R_5$)$R_6$, (3) a compound wherein T is pyridyl which is substituted by $R_2$, Q is thienyl which may be substituted by $R_3$, or pyridyl which may be substituted by $R_3$, $R_1$ is —C(=O)$R_4$, and $R_4$ is alkyl, (4) α-(3,5-dimethoxyphenyl)-β-(2-methoxy-4-methylphenyl)-β-acetoxyacrylonitrile, and (5) α-(3,5-dimethoxyphenyl)-β-(2,6-dimethoxy-4-methylphenyl)-β-acetoxyacrylonitrile, wherein a geometrical isomer has a longer retention time when analyzed by reversed-phase liquid chromatography in which a packing comprising silica having chemically bonded thereto an alkyl group selected from trimethyl, octyl and octadecyl, is used as the stationary phase and a polar solvent selected from water, methanol and acetonitrile is used as the mobile phase, and the geometrical isomer mixture contains the geometrical isomer in a larger proportion, obtained by a process comprising (a) reacting a compound represented by the formula (II):

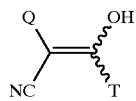

(II)

with a compound represented by the formula (III):

X—$R_1$         (III)

wherein $R_1$ is as defined above, and X is halogen in the presence of a base and a solvent, or (b) isomerizing, under irradiation with light, a geometrical isomer having a shorter retention time when analyzed by the reversed-phase liquid chromatography, or a geometrical isomer mixture containing such geometrical isomer in a larger proportion, to produce the geometrical isomer mixture containing a geometrical isomer in a larger proportion.

5. A process for producing a geometrical isomer of an acrylonitrile compound represented by the formula (I) or of its salt, or a mixture thereof:

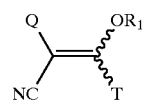

(I)

wherein T is phenyl which is substituted by $R_2$, or pyridyl which is substituted by $R_2$, Q is phenyl which may be substituted by $R_3$, thienyl which may be substituted by $R_3$, pyridyl which may be substituted by $R_3$, or benzyl which may be substituted by $R_3$, $R_1$ is —C(=O)$R_4$ or —C(=S)$R_4$, each of $R_2$ and $R_3$ is halogen, alkyl which may be substituted, alkenyl which may be substituted, alkynyl which may be substituted, alkoxy which may be substituted, alkenyloxy which may be substituted, alkynyloxy which may be substituted, alkythio which may be substituted, alkylsulfinyl which may be substituted, alkylsulfonyl which may be substituted, alkenylthio which may be substituted, alkenylsufinyl which may be substituted, alkenylsulfonyl which may be substituted, alkynylthio which may be substituted, alkynylsulfinyl which may be substituted, alkynylsulfonyl which may be substituted, nitro, cyano, phenyl which may be substituted, phenoxy which may be substituted, phenylthio which may be substituted, phenylsulfinyl which may be substituted, phenylsulfonyl which may be substituted, benzyl which may be substituted, benzyloxy which may be substituted, benzylthio which may be substituted, or benzoyl which may be substituted, $R_4$ is alkyl which may be substituted, alkenyl which may be substituted, alkynyl which may be substituted, alkoxy which may be substituted, alkenyloxy which may be substituted, alkynyloxy which may be substituted, alkylthio which may be substituted, alkenylthio which may be substituted, alkynylthio which may be substituted, cycloalkyl, cycloalkyloxy, cycloalkythio —N($R_5$)$R_6$, phenyl which may be substituted, phenoxy which may be substituted, phenylthio which may be substituted, benzyl which may be substituted, benzyloxy which may be substituted, benzylthio which may be substituted, each of $R_5$ and $R_6$ is hydrogen, alkyl or alkoxy, excluding (1) a compound wherein T is phenyl which is substituted by $R_2$, Q is thienyl which may be substituted by $R_3$, $R_1$ is —C(=O)$R_4$, and $R_4$ is alkyl which may be substituted, alkenyl which may be substituted, alkynyl which may be substituted, alkoxy which may be substituted, alkenyloxy which may be substituted, alkynyloxy which may be substituted, cycloalkyl, cycloalkyloxy, —N($R_5$)$R_6$, phenyl which may be substituted, phenoxy which may be substituted, phenylthio which may be substituted, benzyl which may be substituted, benzyloxy which may be substituted, benzylthio which may be substituted, (2) a compound wherein T is phenyl which is substituted by $R_2$, Q is thienyl which may be substituted by $R_3$, $R_1$ is —C(=S)$R_4$, and $R_4$ is —N($R_5$)$R_6$, (3) a compound wherein T is pyridyl which is substituted by $R_2$, Q is thienyl which may be substituted by $R_3$, or pyridyl which may be substituted by $R_3$, $R_1$ is —C(=O)$R_4$, and $R_4$ is alkyl, (4) α-(3,5-dimethoxyphenyl)-β-(2-methoxy-4-methylphenyl)-β-acetoxyacrylonitrile, and (5) α-(3,5-dimethoxyphenyl)-β-(2,6-dimethoxy-4-methylphenyl)-β-acetoxyacrylonitrile, wherein the geometrical isomer has a longer retention time when analyzed by reversed-phase liquid chromatography in which a packing comprising silica having chemically bonded thereto an alkyl group selected from trimethyl, octyl and octadecyl, is used as the stationary phase and a polar solvent selected from water, methanol and acetonitrile is used as a mobile phase, and the geometrical isomer mixture contains the geometrical isomer in a larger proportion, said process comprising: reacting a compound represented by the formula (IV):

$$Q\text{—}CH_2CN \tag{IV}$$

wherein Q is as defined above,
with a compound represented by the formula (V):

$$T\text{—}COZ \tag{V}$$

wherein T is as defined above, and Z is a halogen or alkoxy, in the presence of a base and a solvent, and then adding and reacting a compound represented by the formula (III):

$$X\text{—}R_1 \tag{III}$$

wherein $R_1$ is as defined above, and X is a halogen, to produce the geometrical isomer having a longer retention time, or the geometrical isomer mixture containing the geometrical isomer in a larger proportion.

6. The geometrical isomer or the geometrical isomer mixture containing such geometrical isomer in a larger proportion, produced by the process of claim 5.

7. The geometrical isomer mixture of claim 4, wherein the process comprises (a).

8. The geometrical isomer mixture of claim 4, wherein the process comprises (b).

9. A pesticide comprising the geometrical isomer mixture of claim 1 as an active ingredient and a carrier or a diluent.

10. A pesticide comprising the geometrical isomer mixture of claim 4 as an active ingredient and a carrier or a diluent.

11. An insecticide, miticide or nematicide comprising the geometrical isomer mixture of claim 1 as an active ingredient and a carrier or a diluent.

12. An insecticide, miticide or nematicide comprising the geometrical isomer mixture of claim 4 as an active ingredient and a carrier or a diluent.

13. A method for controlling a pest, which comprises
applying the geometrical isomer mixture of claim 1 to the pest.

14. A method for controlling a pest, which comprises
applying the geometrical isomer mixture of claim 4 to the pest.

* * * * *